US005540674A

United States Patent [19]

Karas et al.

[11] Patent Number: 5,540,674

[45] Date of Patent: Jul. 30, 1996

[54] SOLUTION CONTAINER WITH DUAL USE ACCESS PORT

[75] Inventors: Peter J. Karas, Libertyville; Timothy J. Oswald, Lincolnshire, both of Ill.

[73] Assignee: Abbott Laboratories, Abbott Park, Ill.

[21] Appl. No.: 127,851

[22] Filed: Sep. 28, 1993

[51] Int. Cl.[6] .......... A61M 5/32

[52] U.S. Cl. .......... 604/415; 604/403; 604/408; 604/411; 604/905; 215/247; 215/249

[58] Field of Search .......... 128/912; 604/82, 604/86–88, 90, 415, 905, 403, 408, 411; 220/254, 257–258; 215/247, 249

[56] References Cited

U.S. PATENT DOCUMENTS

| | | | |
|---|---|---|---|
| 2,906,423 | 9/1959 | Sandhage | 215/249 |
| 3,071,274 | 1/1963 | Ravn | 215/249 |
| 3,358,865 | 12/1967 | Andersen | 215/249 |
| 4,592,092 | 5/1986 | McPhee | 604/415 |

*Primary Examiner*—Randall Green
*Assistant Examiner*—P. Zuttarelli
*Attorney, Agent, or Firm*—A. Nicholas Trausel

[57] ABSTRACT

A parenteral solution container having a dual use access port used for both the administration of fluids to a patient as well as for the addition of fluids to the container, includes a generally cylindrical wall with an axial passage therethrough. A fluid-tight sealing means, having a reseal member that includes a slit therein to enable the reseal member to be pierced with a blunt, metal cannula, or sharp needle is removably attached to the dual use access port. When the dual use access port is used in its fluid addition capacity, the reseal member is attached to the wall and a blunt cannula is passed through the reseal member. Once the blunt cannula has been completely inserted, fluids may be added to the container. To use the dual use access port in its administration capacity, the sealing means is completely removed from the wall. A piercing pin is inserted into the wall creating a fluid-tight seal so that fluids may be administered to a patient.

7 Claims, 2 Drawing Sheets

SOLUTION CONTAINER WITH DUAL USE ACCESS PORT

TECHNICAL FIELD OF THE INVENTION

The present invention generally relates to an infusion container for a parenteral solution for patient administration, and more particularly to a solution container having a dual use access port that can be used for administering solutions to a patient and for adding solutions to the container.

BACKGROUND OF THE INVENTION

Access ports are commonly used in infusion solution containers to administer parenteral solutions to a patient, or to add medicaments or other solutions to the container prior to administration. Current solution containers typically have a dedicated access port for solution administration to a patient and a dedicated access port for the addition of diluent or other ingredients to the container. This type of construction is relatively costly to manufacture since two separate dedicated access ports must be manufactured.

In the dedicated access port for the addition of ingredients to the container, a reseal member is typically used. A reseal member prevents leakage of liquid from within the container after the reseal member is pierced by a cannula or needle to create a passage for the cannula therethrough so that solutions may be added to and mixed with the components in the container.

A typical prior art reseal member is comprised of a generally cylindrical, solid, rubber body. To add solutions, the reseal member is pierced by a sharp cannula or needle. Sharp cannulas or needles are commonly used to penetrate the reseal member because the reseal member is thick and solid at the insertion point.

To promote efficiency in the use of such containers, sharp cannulas or needles are being replaced with blunt cannulas. However, a blunt cannula cannot be inserted in the typical reseal member without application of undesirably high force.

The present invention is directed to a solution container which can be economically manufactured and which is configured for versatile use in connection with preparation and administration of parenteral solutions.

SUMMARY OF THE INVENTION

This invention provides a solution container having a dual use access port for both the administration of solutions in an infusion system to a patient, as well as for the addition of solutions or other components to the container prior to administration. The dual use access port of the present invention may be configured as a down port or a side port of the container.

The solution container includes a container body for containing a parenteral solution. An access port member is provided having a generally cylindrical peripheral wall defining an end open to the exterior of the container body and which has an axial passage therethrough. The access port member is joined with the container body so that the axial passage is in fluid communication with the solution within the container body. The access port member includes a thin, flexible, puncturable membrane extending across the axial passage integrally with the peripheral wall. The membrane is puncturable by an associated blunt cannula or sharp needle and an associated piercing pin.

For adding solutions to the container, the access port member includes sealing means removably (such as frictionally) attached to the open end of the access port member. The sealing means initially seals the open end of the port member. The sealing means may be removed from the access port member so that an associated piercing pin may be inserted in the port member for administration of the solution in the container to a patient. The sealing means includes a rubber reseal member, a thin disc, and a shaped overseal and associated cap, provided in the form of a shaped metallic ferrule having a detachable cap.

The reseal member has a generally cylindrical rubber body, including a proximal end portion and a distal end portion. The proximal end portion of the reseal member is generally at the open end of the port member so that an associated blunt cannula may be inserted through the body. In one embodiment, the distal end of the reseal member is positioned within port member wall. In an alternate embodiment, the cylindrical rubber body of the reseal member generally encases the port member wall. The reseal member includes means, such as at least one axially extending slit, defining a region of the end portion of the rubber body that exhibits a relatively reduced resistance to penetration by a blunt cannula relative to the remaining area of the end portion of the rubber body so that a solution may be added to the container.

The thin disc generally overlays the proximal end of the reseal member for further sealing the access port member. The shaped overseal means removably secures the reseal member to the port member. The overseal means substantially encases an end portion of the reseal proximal end. The overseal means includes a weakened area that may be broken to remove the overseal means from the reseal member.

When the access port is used in its solution addition capacity, the cap is removed from the sealing means leaving the reseal member, disc and a collar-like portion of the shaped ferrule attached to the wall. An associated blunt, metal cannula is passed through the shaped ferrule, disc and reseal member and once the blunt cannula has been completely inserted, solutions may be added to the container.

To use the access port in its administration capacity, the sealing means is completely removed from the wall. A piercing pin is inserted into the wall creating a fluid-tight seal so that solutions may be administered to a patient.

This invention contemplates that a dual use access port eliminates the need for two dedicated access ports as used in the prior art. This invention further contemplates that the dual use access port reduces the cost of manufacturing the parenteral solution container since one access port is eliminated in favor of the dual access port system. The present invention further contemplates that the dual use access port may incorporate a reseal member that may be pierced by a blunt, metal cannula.

These and other objects, features, and advantages of this invention are evident from the following description of a preferred embodiment of this invention with reference to the accompanying drawings.

DETAILED DESCRIPTION OF THE PREFERRED EMBODIMENT

Figure 2:
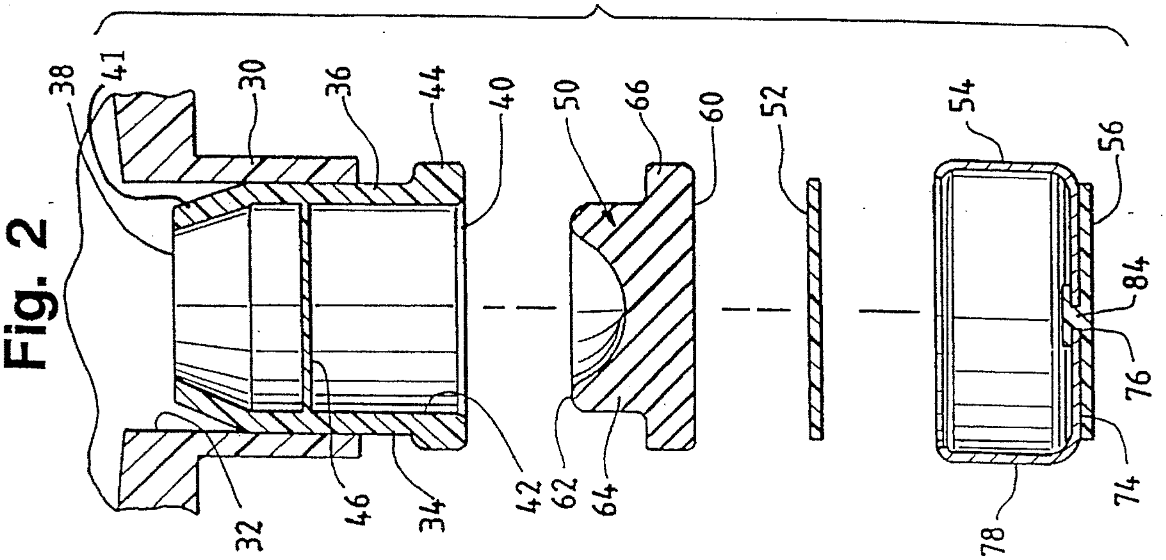
FIG. 2 is a fragmentary exploded view of the sealing means and the dual use access port shown in cross section, according to the present invention.

While the present invention is susceptible of embodiments in various forms, there is shown in the drawings and will hereinafter be described presently preferred embodiments, with the understanding that the present disclosure is to be considered as an exemplification of the invention, and is not intended to limit the invention to the specific embodiments illustrated.

As illustrated in the drawings, a dual use access port 20 in a flexible container 22, illustrated as a flexible parenteral solution container, constitutes a preferred embodiment of the present invention. The dual use access port 20 is used both for administering solutions to a patient and for adding solutions to and mixing with the solutions in the container 22. The dual use access port 20 may be configured as a down port, as illustrated, or a side port (not shown). The container 22 and the body of the dual use access port 20 are made of suitable flexible materials, such as vinyl rubber.

Figure 1:
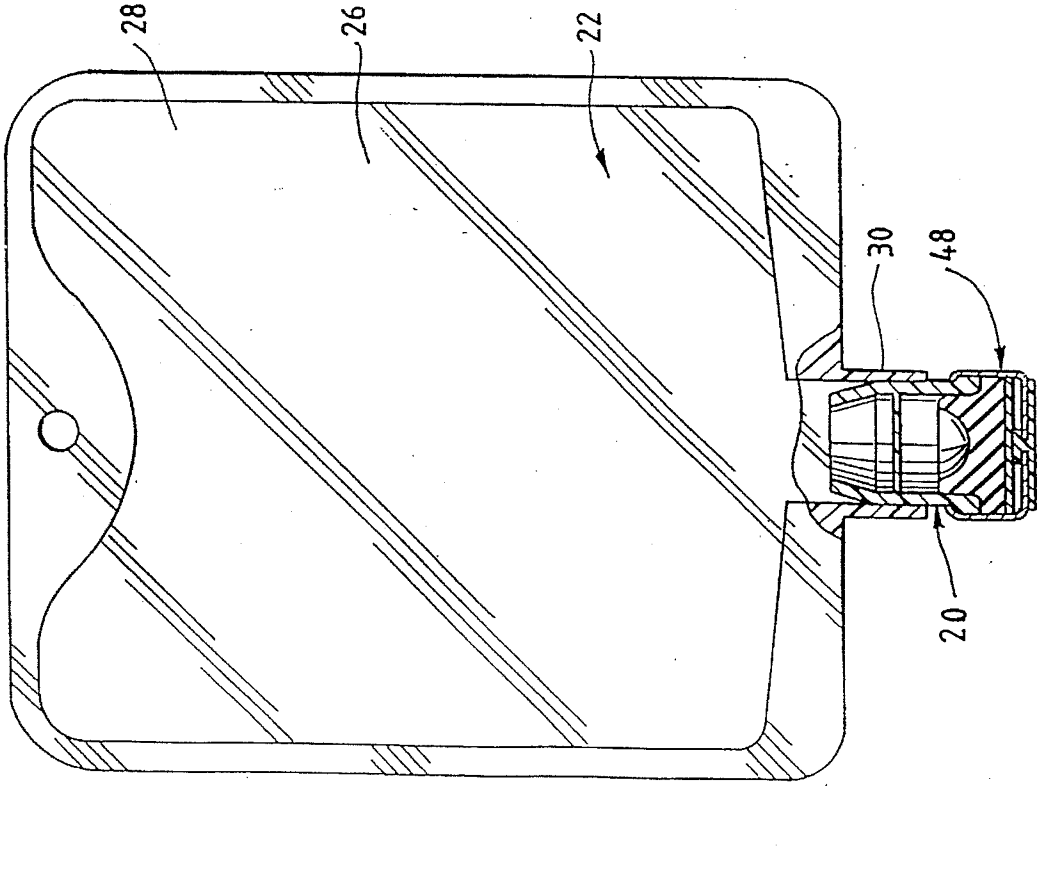
FIG. 1 is an elevational view of a parenteral solution container shown partially in cross-section and having a dual use access port, which includes a sealing means shown in cross-section, attached thereto according to the present invention.

Parenteral solution containers such as 22 are of well known constructions and as such, will not be described in detail herein. Briefly, as shown in FIG. 1, the container 22 includes a container body 26 made of two plastic sheets bonded together by a heat seal 28 along the edges of the sheets. An integrally molded, generally cylindrical tube 30 having a generally cylindrical, axial passage 32 therethrough provides a means for attaching the dual use access port 20 to the container 22.

The dual use access port 20 includes a tubular port member 34 that takes the form of a generally cylindrical wall 36 having open ends 38, 40 and a cylindrical, axial passage 42 therethrough with the distal end at 41. The port member 34 includes an annular shoulder 44 around the circumference of the wall 36 at the proximal end 40. The distal end 38 of the port member 34 is tapered. The port member 34 also includes an integral thin, flexible, nonporous vinyl membrane 46 that extends across the interior circumference of the axial passage 42 to provide a barrier means for fluids.

To insert the port member 34 into the tube 30 of the container 22, the tapered distal end 38 is inserted into the tube 30. The annular shoulder 44 extends outwardly from the distal end of the tube 30. The annular shoulder 44 prevents the port member 34 from being completely inserted into the tube 30. The interior diameter of the tube 30 and the exterior diameter of the wall 36 are approximately the same size and create a fluid-tight seal when the port member 34 is inserted into the tube 30. The port member 34 is attached to the tube 30 by appropriate means, such as by solvent bonding to create a fluid-tight, mechanical-like bond. When the port member 34 is secured to the tube 30, the port member axial passage 42 is in fluid communication with the solution in the container 22.

The novel dual use access port 20 of the present invention includes a sealing means 48 for creating a fluid-tight seal within the port member 34 to provide a barrier for fluids. The sealing means 48 includes a reseal member 50, a disc 52, a shaped overseal or ferrule 54, and a cap 56. The sealing means 48 is removably secured to the port member 34 for reasons that will become clear herein.

The reseal member 50 of the present invention may be configured in any of a variety of forms. The reseal member 50 is made of a soft rubber material, preferably soft gum rubber, so as to be penetrable by an associated conventional smooth, blunt, metal cannula 58. The reseal member 50 is used to seal the port member 34. The cannula 58 may be passed through the reseal member 50 as explained herein to add solutions to the contents of the container. The cannula 58 will not create particulates or tear the interior of the reseal member 50 as it is passed through the reseal member 50 since the cannula 58 is smooth and blunt.

The reseal member 50 may be configured in a variety of shapes. In the embodiment shown in FIGS. 1–4, the reseal member 50 has a proximal end portion 60 and a distal end portion 62, and takes the form of a generally cylindrically shaped body 64 which defines a length and a radius. An annular shoulder 66 extends outwardly around the circumference of the body 64 from the proximal end portion 60. When the reseal member 50 is seated in the port member 34, the distal end portion 62 is within the interior of the wall 36. The proximal end portion 60 is located generally at the open end 40 of the wall 36. The interior diameter of the wall 36 and the exterior diameter of the reseal member 50 are approximately the same size so as to create a fluid-tight fit when the reseal member 50 is inserted into the wall 36. The reseal member 50 is in frictional engagement with the wall 36.

Figure 6:
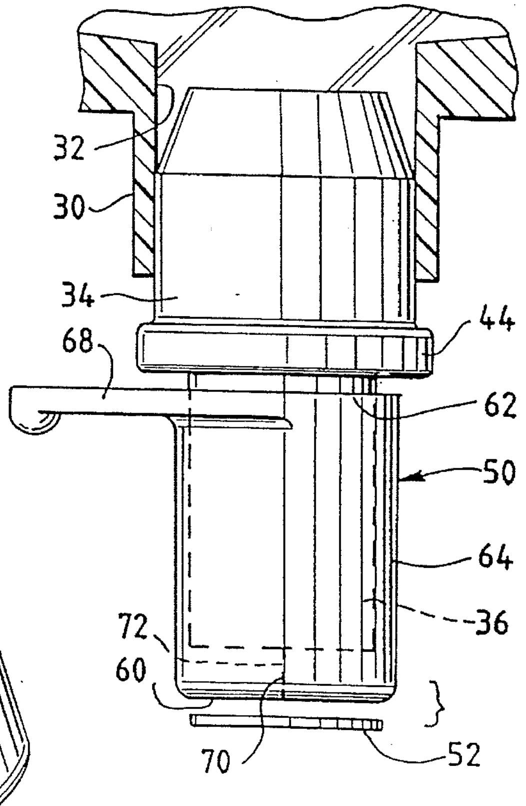
FIG. 6 is an alternate embodiment of a sealing means according to the present invention.

In the embodiment shown in FIG. 6, the reseal member 50 has a cap-like configuration, including a proximal end portion 60 and a distal end portion 62, and takes the form of a generally cylindrically shaped body 64. A handle 68 extends outwardly from the distal end portion 62 of the body 64. The body 64 generally encases the peripheral wall 36 of the port member 34. The interior diameter of the body 64 and the exterior diameter of the wall 36 are approximately the same size to create a fluid-tight fit when the reseal member 50 encases the wall 36. The reseal member 50 is in frictional engagement with the wall 36.

The body 64 of the reseal member 50 includes a region 70 which exhibits a relatively reduced resistance to penetration by a blunt cannula 58 relative to the remaining area of the proximal end portion 60. This region 70 may take the form of a preformed slit, or more than one preformed slit, a molded recess, or a combination of these means. As illustrated in the drawings, the region 70 includes a preformed axially extending slit 72 that extends diametrically across the body 64. When the reseal member 50 of the present invention is used in combination with a blunt, metal cannula 58, a user only meeds to exert a minimal amount of force, approximately three pounds of force, to insert the blunt cannula 58 through the reseal member 50.

Referring again to the embodiment of FIGS. 1–4, the sealing means 48 also includes a disc 52, a shaped overseal 54, and a cap 56. The disc 52 is generally thin, flat and flexible and overlays the proximal end portion 60 of the reseal member 50 and provides an additional barrier means for sealing the port member 34. The disc 52 is bonded to the reseal member 50 by suitable means, such as adhesive, solvent bonding, or the like. Suitable, fluid non-permeable materials, such as foil, film or rubber, are used as materials for the disc 52.

The shaped overseal 54 encases the disc 52, a portion of the reseal member 50 and a portion of the port member wall 36. A suitable protective overseal can be provided in the embodiment of FIG. 6. The shaped overseal 54 initially protects the reseal member 50 and the disc 52 from microbacterial ingress and provides a means for attaching and securing the reseal member 50 and disc 52 to the port member 34. The overseal 54 includes a flat, disc-like, bottom portion 74 having an aperture 76 generally in the center thereof, and an integral, annular depending skirt portion 78. The overseal 54 is made of suitable materials, such as rigid plastic, metal, elastomeric materials or shrink wrap. When the overseal 54 is placed on the port member 34, the inner surface of the bottom portion 74 is adjacent to the disc 52 and the skirt portion 78 encases the disc 52, the annular shoulder 66 of the reseal member 50 and the port member shoulder 44. The distal end 80 of the overseal 54 is crimped, folded, or otherwise shaped around its circumference so as to contact the distal end of the port member shoulder 44 to provide a means for attaching the shaped overseal 54 to the port member wall. Thus, the disc 52 and reseal member 50 are seated within the wall 36 when the overseal 54 is attached to the port member 34. The overseal 54 also includes a means 82 for removing the overseal 54, which will be described in detail herein, to allow a user to remove the sealing means 48 so the dual use access port 20 can be used as an administration port.

The cap 56 is attached to the exterior of the bottom portion 74 of the overseal 54 and is generally disc-shaped with a shaped protruding boss 84 formed in the center thereof. When the cap 56 is attached to the overseal 54, the boss 84 extends through the aperture 76 in the overseal 54 and abuts the proximal end of the disc 52 and the interior of the overseal 54. To allow the reseal member 50 to be accessed by a blunt cannula 58, as described hereinbelow, the cap 56 is removed, tearing a frangible portion of the overseal 54 and thereby opening the aperture in the overseal 54 as shown in FIG. 4.

The cap 56 may be removed in several manners. For example, the cap 56 may be flipped off by pulling on a side of the cap 56 with a sufficient amount of force to tear the overseal 54 thereby creating an enlarged aperture. Alternatively, the cap 56 may be removed by applying torque along with a pulling action.

To insert the blunt, metal cannula 58 through the reseal member 50, the user places the end of the cannula 58 through the enlarged aperture in the overseal 54 and against the disc and pushes the cannula through the disc 52 and the reseal member 50. The blunt cannula 58 will pierce the thin, flexible disc 52 and then pass through the reseal member 50. If a partial slit or a recess is being used, the blunt cannula 58 must penetrate a small, thin, solid portion (not shown) of the reseal body 64 but since the reseal member 50 is made of a soft rubber material, the body 64 is easily penetrated and displaced around the cannula 58. Furthermore, since only a small, thin portion of the body needs to be penetrated, a user need only apply a minimal force to penetrate the body 64. When the cannula 58 passes through the partial slit, or if a full length slit 72 is being used, the body 64 compresses slightly around the slit 72 thereby widening the slit 72 to allow the blunt cannula 58 to pass therethrough.

Figure 4:
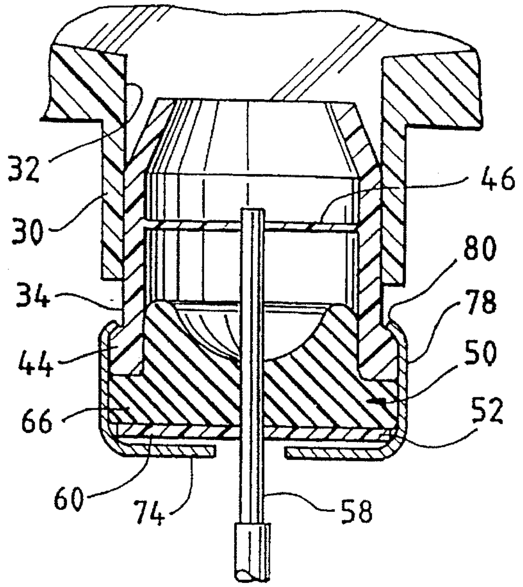
FIG. 4 is an elevational view of the sealing means with a blunt cannula inserted therethrough shown in cross-section and the dual use access port and a portion of the container shown in cross section.

As shown in FIG. 4, the blunt cannula 58 forms a small passage in the disc 52, the reseal member 50 and the membrane 46 when the blunt cannula 58 is inserted therethrough. Once the cannula 58 has been fully inserted through the reseal member 50 and the membrane 46, the reseal body 64 forms a generally fluid-tight seal around the cannula 58 due to the natural resiliency of the gum rubber. After complete insertion, solutions can be passed through the cannula 58 and into the container 22. When the cannula 58 is removed, the body 64 is decompressed and a generally fluid-tight seal is reformed due to the natural resiliency of the rubber.

In order for the dual use access port 20 to be used as an administration port, the sealing means 48 must be removed from the dual use access port 20. As stated above, the overseal 54 includes a means 82 for removing the overseal 54. The removing means 82 can take one of many forms, and this disclosure is not intended to be limited by the means disclosed below.

Figure 3:
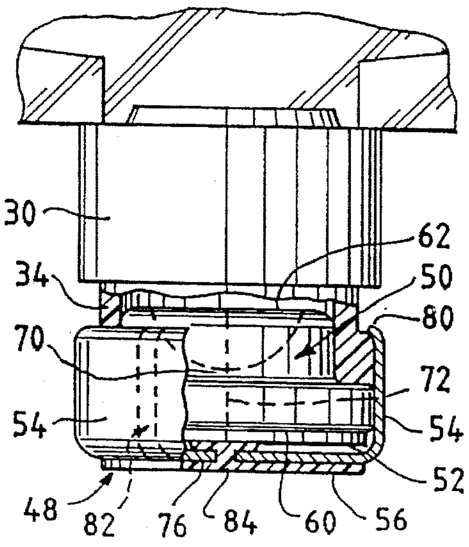
FIG. 3 is an elevational view of the sealing means shown partially in cross-section and the dual use access port and a portion of the container.

As shown in FIG. 3, the removing means 82 takes the form of a weakened area or score line along the length of the skirt portion 78 of the overseal 54. Preferably, this embodiment is used with a metal material, an elastomeric material or with shrink wrap. To remove the overseal 54, the skirt portion 78 is broken along the weakened area. Thereafter, the overseal 54 can be removed leaving the reseal member 50 and disc 52 exposed.

Alternatively, the removing means 82 may take the form of a weakened area that extends around the circumference of the flat, bottom portion 74 of the overseal 54 and extends down the length of the skirt portion 78. A tab (not shown) may be attached to the weakened area. This removing means 82 may be used with a rigid plastic material. To remove the overseal 54, the tab is pulled and travels along the weakened area. Thereafter, the overseal 54 can be removed leaving the reseal member 50 and disc 52 exposed.

After the overseal 54 has been removed, the reseal member 50 and disc 52 are removed. To remove the reseal member 50 and disc 52, a user grasps the proximal end 60 of the reseal member 50 and applies a force sufficient to overcome the frictional force between the reseal member 50 and the wall 36. For example, a user may overcome this frictional force by applying a twisting motion to remove the reseal member 50.

Figure 5:
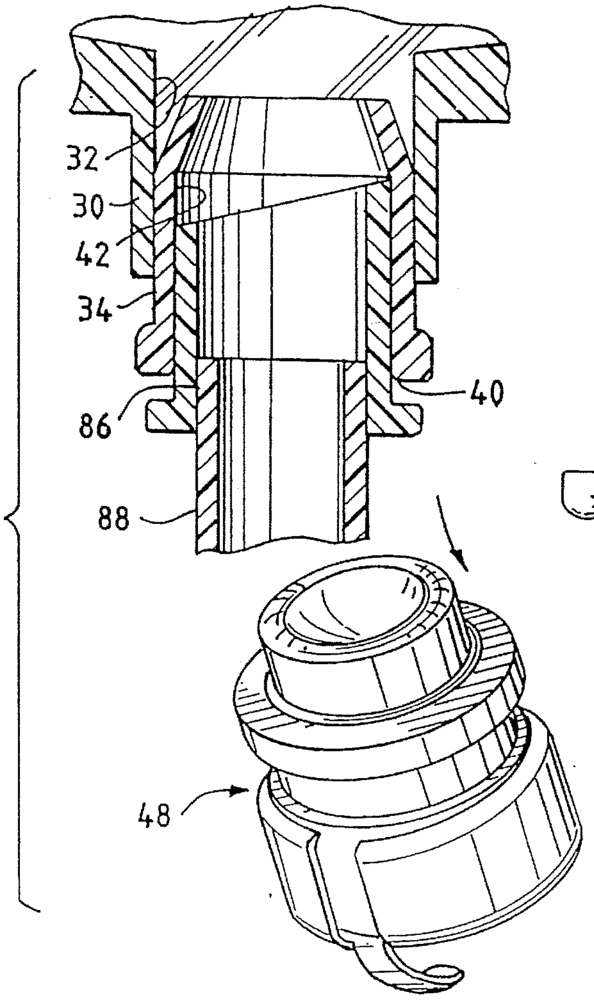
FIG. 5 is an elevational view of a portion of the container, the access port and a piercing pin inserted therethrough, with the sealing means shown removed.

As shown in FIG. 5, once the sealing means 48 has been removed, a conventional piercing pin or spike 86, with attached tubing 88, may be inserted into the dual use access port 20. When fully inserted, the piercing pin 86 ruptures the membrane 46. The piercing pin 86 and the interior of the wall 36 are approximately the same diameter so a fluid-tight seal is achieved. Thereafter, the solutions within the container 20 may be administered to a patient by conventional methods.

From the foregoing, it will be observed that numerous modifications and variations can be effected without departing from the true spirit and scope of the novel concept of the present invention. It is to be understood that no limitation with respect to the specific embodiments is intended or should be inferred. The disclosure is intended to cover by the appended claims all such modifications as fall within the scope of the claims.

The invention claimed is:

1. A parenteral solution container having a dual use access port for alternative use with an associated small diameter cannula and an associated larger diameter piercing pin, comprising:

a container body for containing a parenteral solution for patient administration;

an access port member having a generally cylindrical peripheral wall defining a proximal end open to the exterior of said container body and a distal end open to the interior of said container and an axial passage therethrough, said distal end having an inwardly tapering inner surface, said access port member being joined with said container body so that said axial passage is in fluid communication with the solution within the container body, said access port member including a thin, flexible, puncturable membrane sealingly extending across the axial passageway integrally with the peripheral wall; and sealing means removably attached to said open end of said access port member for initially sealing said open end, said sealing means including a rubber reseal member having a generally cylindrical rubber body, a proximal end and a distal end, said proximal end positioned generally at the open end of said peripheral wall to permit insertion of the associated cannula through said body, said distal end positioned within the peripheral wall, and said cylindrical rubber body generally encased by the peripheral wall, said reseal member including means for relatively reduced resistance to penetration by the associated cannula for addition of a solution into said container, said sealing means thereafter being removable from said access port member to permit insertion of the associated piercing pin sealingly within the tapered inner surface of the distal end of the access port member for delivery administration of the solution from said container.

2. A parenteral solution container having a dual use access port as defined in claim 1, wherein said means for relatively reduced resistance to penetration by a cannula includes at least one axially extending slit.

3. A parenteral solution container having a dual use access port as defined in claim 2, wherein said sealing means further includes a thin disc generally overlaying the proximal end of said reseal member for further sealing said access port member.

4. A parenteral solution container having a dual use access port as defined in claim 3, wherein said sealing means further includes a shaped overseal means for removably securing said reseal member to said port, said overseal means substantially encasing an end portion of said reseal proximal end, said overseal means being removable from said reseal member.

5. A parenteral solution container having a dual use access port as defined in claim 4, wherein said overseal means includes a weakened area that may be broken to remove the overseal-means from the reseal member.

6. An infusion system comprising:

a container body for containing a parenteral solution for patient administration;

an access port member having a generally cylindrical peripheral wall defining a proximal end open to the exterior of said container body and a distal end open to the interior of said container and an axial passage therethrough, said distal end having an inwardly tapered inner surface, said access port member being joined with said container body so that said axial passage is in fluid communication with the solution within the container body, said access port member including a thin, flexible, puncturable membrane sealingly extending across the axial passageway integrally with the peripheral wall;

sealing means frictionally attached to said open end of said access port member for initially sealing said open end, said sealing means including a rubber reseal member and a thin disc;

said reseal member having a generally cylindrical rubber body, a proximal end and a distal end, the proximal end positioned generally at the open end of said wall to permit insertion of an associated needle through said body, means for reduced resistance to penetration by an insertable member, said disc overlaying the proximal end of said reseal member for further sealing said access port member;

a cannula insertable through said disc and said rubber body for adding fluids to the solution in the container; and a piercing pin insertable into said access port after said sealing means has been removed from said access port so as to seal with the tapered inner surface of the distal end of the access port for administration of the solution in said container.

7. An infusion system as defined in claim 6, wherein said sealing means further includes a shaped overseal means for removably securing said reseal member to said port, said overseal means substantially encasing an end portion of said reseal proximal end, said overseal means being removable from said reseal member.

* * * * *